United States Patent [19]

Yamada et al.

[11] Patent Number: 5,347,025

[45] Date of Patent: Sep. 13, 1994

[54] CATALYST FOR POLYMERIZATION OF VINYL COMPOUND

[75] Inventors: Satoru Yamada; Akihiro Yano, both of Mie, Japan

[73] Assignee: Tosoh Corporation, Shinnanyo, Japan

[21] Appl. No.: 117,290

[22] Filed: Sep. 7, 1993

[30] Foreign Application Priority Data

Sep. 9, 1992 [JP] Japan .................................. 4-265527

[51] Int. Cl.$^5$ .............................................. C07F 7/28
[52] U.S. Cl. ........................................ 556/11; 556/12; 556/19; 556/28; 556/53; 502/155; 526/127; 526/160
[58] Field of Search ..................... 556/11, 12, 28, 53, 556/19; 526/160

[56] References Cited

U.S. PATENT DOCUMENTS 4,607,112  8/1986  Grubbs et al. .
5,171,871 12/1992  Miyashita .............................. 556/27

FOREIGN PATENT DOCUMENTS 1191374  4/1965  Fed. Rep. of Germany .

OTHER PUBLICATIONS

J. Am. Chem. Soc., vol. 102, May 9, 1980 "Titanium Metallacarbene–Metallacyclobutane Reactions: Stepwise Metathesis", Alistair Lees and Arthur Adamson, pp. 6876–6878.

*Primary Examiner*—Joseph L. Schofer
*Assistant Examiner*—David Wu
*Attorney, Agent, or Firm*—Oblon, Spivak, McClelland, Maier & Neustadt

[57] ABSTRACT

A novel catalyst for polymerization of a vinyl compound is provided which comprises, as a catalyst component (A), an organometal complex represented by General Formula (1) below:

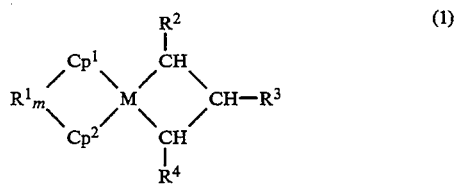

where $Cp^1$ and $Cp^2$ are independently a substituted or unsubstituted cyclopentadienyl group; $R^1$ is a group selected from alkylene groups or arylalkylene groups having 1 to 20 carbons, dialkylsillylene groups, dialkylgermanylene groups, alkylphosphinediyl groups, or alkylimino groups and $R^1$ crosslinking $Cp^1$ and $Cp^2$ together; m is 0 or 1; M is titanium, zirconium, or hafnium; and $R^2$, $R^3$, and $R^4$ are independently hydrogen hydrocarbon group of 1 to 12 carbons, an alkoxy group, or an aryloxy group, and a catalyst component (B) represented by the general formula (2) or (3)

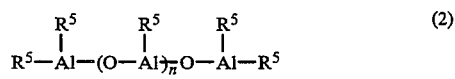

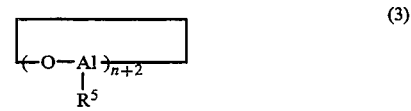

where n is an integer of from 4 to 60, and $R^5$ is a hydrocarbon group. A process for producing a vinyl compound polymer which employs the catalyst defined above is also provided.

3 Claims, No Drawings

CATALYST FOR POLYMERIZATION OF VINYL COMPOUND

BACKGROUND OF THE INVENTION

1. Field of the Invention

The present invention relates to a catalyst for producing a polymer of a vinyl compound (including α-olefin polymers and aromatic compound polymers), and a process for producing a vinyl compound polymer employing the catalyst. More particularly, the present invention relates to a process for producing an aromatic vinyl compound polymer having mainly syndiotactic structure with high catalyst activity and with high selectivity.

2. Description of the Related Art

Aromatic Vinyl compound polymers include three structure types of polymers: syndiotactic polymers, isotactic polymers, and atactic polymers.

Of these, the polymers of the syndiotactic structure, which have a high melting point and crystallize quickly in comparison with polymers of other structures, are useful as heat-resistant polymers. The syndiotactic aromatic vinyl compound polymer is produced, for example, in the presence of a catalyst formed by contact of a titanium compound such as titanium halide and alkoxytitanium with an organoaluminum compound such as methylalumoxane as disclosed in Japanese Patent Application Laid-Open No. 62-04818.

However, in the polymerization of styrene monomer with a catalyst system constituted of a combination of a titanium compound such as titanium tetrachloride and tetraethoxytitanium with methylalumoxane, the catalyst activity is low, and the catalyst remains in the formed polymer in a considerable amount. Therefore the polymer is presumed to discolors significantly during high-temperature molding, and not to be suitable for practical use.

On the other hand, a catalyst system composed of methylalumaxane and complex obtained by reaction of a transition metal compound, like titanium tetrachloride, with an organic compound, like 2.2'-dihydroxy-3.3'-di-tert-butyl-5.5'-dimethyl-diphenylsulbide gives a slightly lower content of stereoregular polymer owing chiefly to atactic polymer formation as a by-product even though the catalyst exhibits considerably high catalytic activity. The amorphous polymer coexisting in a larger amount affects adversely the melting point and the crystallization velocity of the polymer. Therefore, removal of the amorphous polymer is required by solvent extraction or the like treatment, disadvantageously.

After comprehensive investigation, it was found by the present inventors that a specific organometal complex in combination of methylalumoxane enables production of aromatic vinyl compound polymers of syndiotactic structure with high catalyst activity and high selectivity, and the present invention has been completed.

SUMMARY OF THE INVENTION

The present invention intends to provide a catalyst for producing a vinyl compound polymer. More particularly, the present invention intends to provide a catalyst for producing an aromatic vinyl compound polymer of syndiotactic structure with high catalyst activity and high selectivity.

The catalyst for polymerization of a vinyl compound of the present invention comprises, as a catalyst component, a novel organometal complex represented by the general formula (1) below:

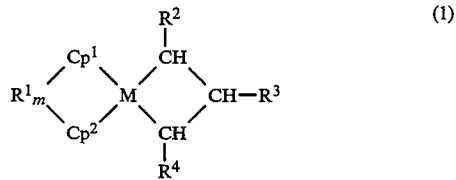

where $Cp^1$ and $Cp^2$ are independently a substituted or unsubstituted cyclopentadienyl group; $R^1$ is a group selected from alkylene groups or arylalkylene groups having 1 to 20 carbons, dialkylsillylene groups, dialkylgermanylene groups, alkylphosphinediyl groups, or alkylimino groups, and $R^1$ crosslinking $Cp^1$ and $Cp^2$ together; m is 0 or 1; M is titanium, zirconium, or hafnium; and $R^2$, $R^3$, and $R^4$ are independently hydrogen a hydrocarbon group of 1 to 12 carbons, an alkoxy group, or an aryloxy group.

The catalyst for polymerization of a vinyl compound of the present invention comprises a catalyst component (A) represented by the general formula (1) above, and a catalyst component (B) represented by the general formula (2) or (3)

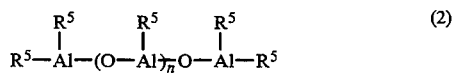

where n is an integer of from 4 to 60, and $R^5$ is a hydrocarbon group.

The present invention further provides a process for producing stereoregular aromatic vinyl compound polymer of high syndiotacticity with high selectivity by use of the above catalyst.

DETAILED DESCRIPTION OF THE PREFERRED EMBODIMENT

The catalyst component (A) of the catalyst for polymerization of a vinyl compound of the present invention can be prepared by reacting the organometal compound represented by the general formula (4) or (5) with an α-olefin represented by the general formula (6);

General Formula (4)

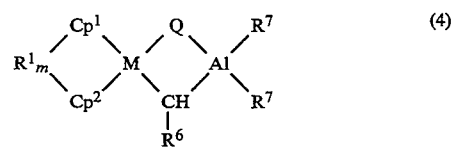

where $Cp^1$ and $Cp^2$ are independently a substituted or unsubstituted cyclopentadienyl group; $R^1$ is a group selected from alkylene groups, or arylalkylene groups having 1 t to 20 carbons, dialkylsilylene groups, dialkylgermanylene groups, alkylphosphinediyl groups, or alkylimino groups, and $R^1$ crosslinking $Cp^1$ and $Cp^2$ together; m is 0 or 1; Q is a hydrocarbon group of 1 to 12 carbons or a halogen atom; $R^6$ is hydrogen, a hydrocarbon group of 1 to 12 carbons, an alkoxy group, or an aryloxy group; $R^7$ is hydrogen or a hydrocarbon group of 1 to 12 carbons, and M is titanium, zirconium, or hafnium;

General Formula (5)

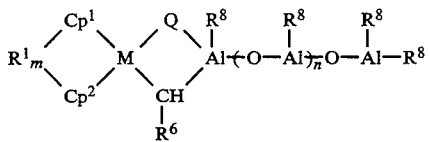

where $Cp^1$ and $Cp^2$ are independently a substituted or unsubstituted cyclopentadienyl group; $R^1$ is a group selected from alkylene groups or arylalkylene groups having 1 to 20 carbons, dialkylsillylene groups, dialkylgermanylene groups, alkylphosphinediyl groups, or alkylimino groups, and $R^1$ crosslinking $Cp^1$ and $Cp^2$ together; m is 0 or 1; Q is a hydrocarbon group of 1 to 12 carbons or a halogen atom; $R^6$ is hydrogen, a hydrocarbon group of 1 to 12 carbons, an alkoxy group, or an aryloxy group; $R^8$ is hydrogen or a hydrocarbon group of 1 to 12 carbons; n is an integer of from 4 to 60; and M is titanium, zirconium, or hafnium;

General Formula (6)

where $R^9$ is hydrogen or a hydrocarbon group of 1 to 12 carbons.

The component represented by the general formula (4) used for synthesis of the catalyst component (A) of the present invention includes specifically (μ-chloro)(μ-methylene)bis(cyclopentadienyl)(dimethylaluminum)-titanium, (μ-chloro)(μ-methylene)methylenebis(cyclopentadienyl)(dimethylaluminum)titanium, (μ-chloro)(μ-methylene)dimethylsilylbis(cyclopentadienyl)-(dimethylaluminum)titanium, (μ-chloro) (μ-methylene)isopropylidenebis(cyclopentadienyl)(dimethylaluminum)titanium, and the like.

The component represented by the general formula (5) used for synthesis of the catalyst component (A) of the present invention includes bis(cyclopentadienyl)-titanium-methylalumoxane complex, methylenebis(cyclopentadienyl)titanium-methylalumoxane complex, dimethylsilylbis(cyclopentadienyl)titanium-methylalumoxane complex, isopropylidenebis(cyclopentadienyl)titaniummethylalumoxane complex, and the like.

The component represented by the general formula (6) used for synthesis of the catalyst component (A) of the present invention includes ethylene, propylene, 1-butene, 1-hexene, 1-octene, styrene, methystyrene, chlorostyrene, methoxystyrene, and the like.

The reaction of the compound of the general formula (4) or (5) with the compound of the general formula (6) is conducted generally in the presence of a solvent.

The molar ratio of the compound of the general formula (4) or (5) to the compound of the general formula (6) is not limited. However, the molar ratio of the compound of the general formula (4) to the compound of the general formula (6) is preferably in the range of from 1:0.5 to 1:10, more preferably from 1:1 to 1:3. The molar ratio of the compound of the general formula (5) to the compound of the general formula (6) is preferably in the range of from 1:0.5 to 1:30, more preferably from 1:1 to 1:10.

The solvent used includes halogenated hydrocarbons such as chloroform and carbon tetrachloride, and aromatic hydrocarbons such as benzene, toluene, and xylene.

The reaction temperature depends on the starting material, the solvent, and other conditions, and is usually in the range of from −50° to 60° C.

The intended compound can be isolated in high purity from the resulting reaction mixture by removing the solvent by vacuum evaporation and recrystallizing the evaporation residue from an organic solvent such as ether.

The catalyst component (A) is confirmed to have the structure of the general formula (1) by proton nucleomagnetic resonance spectroscopy.

The catalyst component (B) is an aluminoxane represented by the general formula (2) or (3). The substituent on the aluminum of the aluminoxane is a hydrocarbon group of 1 to 6 carbons such as methyl, ethyl, propyl, and butyl; preferably methyl. The oligomerization degree is from 6 to 62. This type of compound may be prepared by a known method, for example, by causing reaction by adding an aluminum compound into a suspension of a crystallization water-containing salt (e.g. copper sulfate hydrate, aluminum sulfate hydrate, etc.) in a hydrocarbon medium.

The ratio of the catalyst component (B) to the catalyst component (A), namely (B)/(A), is in the range of from 10 to 1000 in terms of molar ratio.

The vinyl compound polymerizable according to the present invention includes α-olefins, styrene, and derivatives thereof. The derivatives of styrene include alkylstyrenes such as methylstyrene, ethylstyrene, and dimethylstyrene; halogenated styrenes such as chlorostyrene, bromostyrene, and fluorostyrene; halogen-substituted alkylstyrenes such as chloromethylstyrene; alkoxystyrenes such as methoxystyrene; carboxymethylstyrene, alkylsilylstyrene, and the like.

The vinyl compound is polymerized in the presence of the above catalyst. The polymerization may be conducted in bulk, or in an aliphatic hydrocarbon such as pentane, hexane, or heptane, or in an aromatic hydrocarbon such as benzene, toluene, and xylene.

The concentration of the catalyst component used in the solution is preferably in the range of from 0.1 to 1000 mmol/l. The polymerization temperature is not specially limited, but is usually in the range of from −78° to 150° C.

The present invention is described in more detail by reference to Examples without limiting the invention thereto in any way.

EXAMPLE 1

Synthesis of Methylenebis(cyclopentadienyl)-2-phenyltitanacyclobutane Complex

One gram of (μ-chloro)(μ-methylene)methylenebis(-cyclopentadienyl)(dimethylaluminum)titanium was dissolved in 6 ml of toluene, and thereto 0.36 g of styrene was added. The mixture was stirred at room temperature. Then 0.47 g of dimethylaminopyridine was added to the reaction system, whereby precipitate was formed gradually. The suspension was filtered with celite to obtain a red solution. The solution was evaporated to dryness to obtain a reddish brown solid. This solid was dissolved in ether, and left standing at −30° C. for 4 days. Thereby red needle-crystalline methylenebis(cyclopentadienyl)-2-phenyltitanacyclobutane was obtained in a yield of 0.3 g.

The resulting complex was identified by $^1$H-NMR as follows: 0.1 ppm (m, —CH$_2$—), 1.8 ppm (m, Ti—CH$_2$—), 2.1 ppm (t, —(C$_6$H$_5$)CH—), 2.5 ppm (s, Cp—CH$_2$—Cp), 4.7 ppm (t, Cp), and 6.8 ppm (t, Cp).

EXAMPLE 2

Synthesis of Methylenebis(cyclopentadienyl)-3methyltitanacyclobutane Complex

The synthesis was conducted in the same manner as in Example 1 except that propylene was bubbled into the solution in place of addition of styrene. Consequently, red crystalline methylenebis-(cyclopentadienyl)-3-methyltitanacyclobutane was obtained in a yield of 40%.

The resulting complex was identified by $^1$H-NMR as follows: 0.03 ppm (m, CH), 0.7 ppm (s, CH$_3$), 2.3–3.2 ppm (m, Ti—CH$_2$—C), 2.4 ppm (s, Cp—CH$_2$—Cp), 4.7 ppm (t, Cp), and 6.7 ppm (t, Cp).

EXAMPLE 3

Synthesis of Methylenebis(cyclopentadienyl)-2-phenyltitanacyclobutane Complex

In 20 ml of toluene, was dissolved 5g of methylenebis(cyclopentadienyl)-methylalumoxane complex. Styrene (10 equivalents) was added thereto, and the mixture was cooled to −20° C. with stirring. To the resulting red solution, a solution of methylalumoxane (50 equivalent) in toluene was added dropwise gradually. The mixture was then brought to room temperature in 12 hours. The reaction solution was cooled to 0° C. The insoluble matter was removed by filtration with celite, and the filtrate was evaporated dryness. The evaporation residue was dissolved in ether, and the solution was left standing at −40° C. for 5 days. As the result, red crystalline methylenebis(cyclopentadienyl)-2-phenyltitanacyclobutane in a yield of 0.8 g.

EXAMPLE 4

In a nitrogen-purged Shlenk reaction vessel, was placed 0.039 mmol of methylenebis(cyclopentadienyl)-2-phenyltitanacyclobutane prepared in Example 1. Thereto 10 ml of toluene was added. Further thereto, 6 ml of styrene was added. To the mixture, a solution of methylalumoxane (16-mer) in toluene was added dropwise in an amount to give the Al/Ti molar ratio of 200. The reaction was allowed to proceed at 30° C. for 10 hours. Then 10 ml of methanol-hydrochloric acid solution was added to stop the reaction. The resulting white polymer was collected by filtration, and dried to obtain 4.5 g of a polymer.

This polymer was extracted with methyl ethyl ketone by Soxhlet extraction. The polymer was found to contain a methyl ethyl ketone-soluble portion in an amount of 3%.

The melting point of the resulting polymer had a melting point of 267° C. by DSC measurement. The polymer had pentad rrrr of 97%, according to $^{13}$C-NMR structure analysis in o-dichlorobenzene, from the peak of 145.5 ppm resulting from syndiotactic structure.

COMPARATIVE EXAMPLE 1

The polymerization was conducted in the same manner as in Example 4 except that 0.041 mmol of methylenebis(cyclopentadienyl)titanium dichloride was used in place of methylenebis(cyclopentadienyl)-2phenyltitanacyclobutane. As the result, the amount of the formed dry polymer was 0.9 g. This polymer was extracted with methyl ethyl ketone by Soxhlet extraction and was found to have methyl ethyl ketone-soluble portion in an amount of 8%

As shown above, the catalyst of the present invention enables the production of a highly syndiotactic aromatic vinyl compound polymer with high catalyst activity with high selectivity.

What is claimed is:

1. An organometal complex represented by General Formula (1) below:

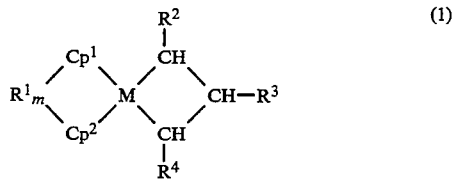

where Cp$^1$ and Cp$^2$ are independently a cyclopentadienyl group; R$^1$ is a group selected from alkylene groups or arylalkylene groups having 1 to 20 carbons, dialkylsillylene groups, dialkylgermanylene groups, alkylphosphinediYl groups, or alkylimino groups, and R$^1$ crosslinking Cp$^2$ together; m is 0 or 1; M is titanium, zirconium, or hafnium; and R$^2$, R$^3$, and R$^4$ are independently hydrogen, a hydrocarbon group of 1 to 12 carbons, an alkoxy group, or an aryloxy group.

2. A organometal complex according to claim 1, wherein M is titanium, R$^2$ is phenyl, and R$^3$ and R$^4$ are respectively hydrogen.

3. A organometal complex according to claim 1, wherein M is titanium, R$^3$ is methyl, and R$^2$ and R$^4$ are respectively hydrogen.

* * * * *